US00PP25179P2

(12) United States Plant Patent
Isobe

(10) Patent No.: US PP25,179 P2
(45) Date of Patent: Dec. 16, 2014

(54) ***CALIBRACHOA* PLANT NAMED 'SUNBELKU 3382'**

(50) Latin Name: ***Calibrachoa* sp.**
Varietal Denomination: Sunbelku 3382

(71) Applicant: Yasuko Isobe, Shiga (JP)

(72) Inventor: Yasuko Isobe, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 101 days.

(21) Appl. No.: 13/815,122

(22) Filed: Jan. 31, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. A. Whealy

(57) ABSTRACT

A new and distinct cultivar of *Calibrachoa* plant named 'Sunbelku 3382', characterized by its upright to trailing plant habit; vigorous growth habit; freely branching habit; freely flowering habit; long flowering period; relatively large white-colored flowers; and good garden performance.

1 Drawing Sheet

Botanical designation: *Calibrachoa* sp.
Cultivar denomination: 'SUNBELKU 3382'.

BACKGROUND OF THE INVENTION

The present invention relates to a new and distinct cultivar of *Calibrachoa* plant, botanically known as *Calibrachoa* sp. and hereinafter referred to by the name 'Sunbelku 3382'.

The new *Calibrachoa* plant is a product of a planned breeding program conducted by the Inventor in Higashiomi, Shiga, Japan. The objective of the breeding program is to develop new trailing and freely branching *Calibrachoa* plants with numerous large and attractively colored flowers.

The new *Calibrachoa* plant originated from a cross-pollination conducted by the Inventors in Higashiomi, Shiga, Japan in June, 2007 of a proprietary selection of *Calibrachoa* sp. identified as code number 8138, not patented, as the female, or seed, parent with a proprietary selection of *Calibrachoa* sp. identified as code number 4055-12, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in July, 2008.

Asexual reproduction of the new *Calibrachoa* plant by vegetative cuttings in a controlled greenhouse environment in Higashiomi, Shiga, Japan since July, 2008 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunbelku 3382'. These characteristics in combination distinguish 'Sunbelku 3382' as a new and distinct *Calibrachoa* plant:

1. Upright to trailing plant habit.
2. Vigorous growth habit.
3. Freely branching habit.
4. Freely flowering habit.
5. Long flowering period.
6. Relatively large white-colored flowers.
7. Good garden performance.

Plants of the new *Calibrachoa* can be compared to plants of the female parent selection. Plants of the new *Calibrachoa* differ primarily from plants of the female parent selection in internode length as plants of the new *Calibrachoa* have shorter internodes than plants of the female parent selection.

Plants of the new *Calibrachoa* can be compared to plants of the male parent selection. Plants of the new *Calibrachoa* differ primarily from plants of the male parent selection in the following characteristics:

1. Plants of the new *Calibrachoa* are more trailing in plant habit than plants of the male parent selection.
2. Plants of the new *Calibrachoa* have longer internodes than plants of the male parent selection.

Plants of the new *Calibrachoa* can also be compared to plants of *Calibrachoa* 'Suncalho', disclosed in U.S. Plant Pat. No. 21,810. In side-by-side comparisons conducted in Higashiomi, Shiga, Japan, plants of the new *Calibrachoa* and 'Suncalho' differed primarily in the following characteristics:

1. Plants of the new *Calibrachoa* were not as compact as plants of 'Suncalho'.
2. Plants of the new *Calibrachoa* were more trailing than and not as mounding as plants of 'Suncalho'.
3. Plants of the new *Calibrachoa* had longer internodes than plants of 'Suncalho'.
4. Plants of the new *Calibrachoa* had smaller leaves than plants of 'Suncalho'.
5. Plants of the new *Calibrachoa* were more freely flowering than plants of 'Suncalho'.
6. Plants of the new *Calibrachoa* had smaller flowers than plants of 'Suncalho'.

7. Plants of the new *Calibrachoa* had shorter peduncles than plants of 'Suncalho'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbelku 3382' grown in a container.

The photograph at the bottom of the sheet is a close-up view of a typical flowering plant of 'Sunbelku 3382'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Sunbelku 3382'.

Parentage:

*Female, or seed, parent*.—Proprietary selection of *Calibrachoa* sp. identified as code number 8138, not patented.

*Male, or pollen, parent*.—Proprietary selection of *Calibrachoa* sp. identified as code number 4055-12, not patented.

Propagation:

*Type*.—By vegetative cuttings.

*Time to initiate roots, summer*.—About one week at 15° C. to 20° C.

*Time to produce a rooted young plant, summer*.—About three weeks at 15° C. to 20° C.

*Root description*.—Fibrous; white in color.

*Rooting habit*.—Freely branching; medium density.

Plant description:

*Plant and growth habit*.—Initially upright to trailing plant habit; freely branching habit with numerous lateral branches developing per plant; pinching enhances lateral branch development; vigorous growth habit.

*Plant height*.—About 11.5 cm.

*Plant diameter*.—About 51.3 cm.

Lateral branch description:

*Length*.—About 39 cm.

*Diameter*.—About 1.5 mm.

*Internode length*.—About 1.6 cm.

*Strength*.—Strong.

*Aspect*.—Mostly outward.

*Texture*.—Pubescent.

*Color*.—Close to 144B.

Foliage description:

*Arrangement*.—Alternate, simple

*Length*.—About 3.5 cm. .

*Width*.—About 1.3 cm.

*Shape*.—Spatulate.

*Apex*.—Obtuse.

*Base*.—Cuneate.

*Margin*.—Entire.

*Texture, upper and lower surfaces*.—Pubescent.

*Venation pattern*.—Pinnate; reticulate.

*Color*.—Developing leaves, upper surface: Close to 143B. Developing leaves, lower surface: Close to 143C. Fully expanded leaves, upper surface: Close to 143A; venation, close to N144A. Fully expanded leaves, lower surface: Close to 143B; venation, close to 144C.

*Petiole*.—Length: About 4.7 mm. Diameter: About 0.4 mm. Texture, upper and lower surfaces: Sparsely pubescent. Color, upper and lower surfaces: Close to 143C.

Flower description:

*Flower arrangement and habit*.—Single salverform flowers arising from upper leaf axils; freely flowering habit with usually about 135 flowers developing per plant; flowers face upright or outwardly.

*Fragrance*.—None detected.

*Natural flowering season*.—Early flowering habit, plants of the new *Calibrachoa* initiate and develop flowers about three to four weeks after planting; long flowering period, flowering naturally commences during the spring and plants flower continuously throughout the summer until late autumn in Japan.

*Flower longevity*.—Individual flowers last about seven to ten days on the plant; flowers not persistent.

*Flower diameter*.—About 2.9 cm.

*Flower length (depth)*.—About 2.8 cm.

*Throat diameter*.—About 8.1 mm.

*Tube length*.—About 1.6 cm.

*Tube diameter, base*.—About 3.2 mm.

*Flower buds*.—Shape: Cylindrical. Length: About 2.2 cm. Diameter: About 4.3 mm. Color: Close to 1D; venation, close to N167A.

*Corolla*.—Arrangement: Five petals fused at the base and opening into a flared trumpet. Petal length from throat: About 1.1 cm. Petal width: About 1.2 cm. Petal shape: Roughly spatulate. Petal apex: Rounded with truncate tendencies. Petal margin: Entire. Petal texture, upper and lower surfaces: Smooth, glabrous. Throat texture: Smooth, glabrous. Tube texture: Pubescent. Color: Petal, when opening, upper and lower surfaces: Close to NN155D. Petal, fully opened, upper surface: Close to NN155D; venation, close to N144A. Petal, fully opened, lower surface: Close to 1D; venation, close to 1D. Throat: Close to 1B; venation, close to N144A. Tube: Close to 1D; venation, close to N144A and N167A.

*Calyx*.—Arrangement: One star-shaped tubular calyx tube with five sepals fused at the base. Sepal length: About 5.5 mm to 8.8 mm. Sepal width: About 2.2 mm. Sepal shape: Lanceolate. Sepal apex: Obtuse. Sepal margin: Entire. Sepal texture, upper and lower surfaces: Pubescent. Sepal color: Immature and mature, upper surface: Close to 143C. Immature and mature, lower surface: Close to 143B. Peduncles: Length: About 9.1 mm. Diameter: About 0.6 mm. Angle: Mostly outwardly. Strength: Strong. Texture: Pubescent. Color: Close to 144B.

*Reproductive organs*.—Stamens: Quantity: Five per flower. Stamen length: About 4.7 mm to 8.8 mm. Anther shape: Ellipsoidal. Anther size: About 1.2 mm by 1.4 mm. Anther color: Close to 5D. Pollen amount: Moderate. Pollen color: Close to 4C. Pistils: Quantity: One per flower. Pistil length: About 8.9 mm. Style color: Close to 144D. Stigma shape: Transversely ellipsoidal. Stigma color: Close to 144C. Ovary color: Close to 144D.

*Seeds and fruits*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Sunbelku 3382' as illustrated and described.

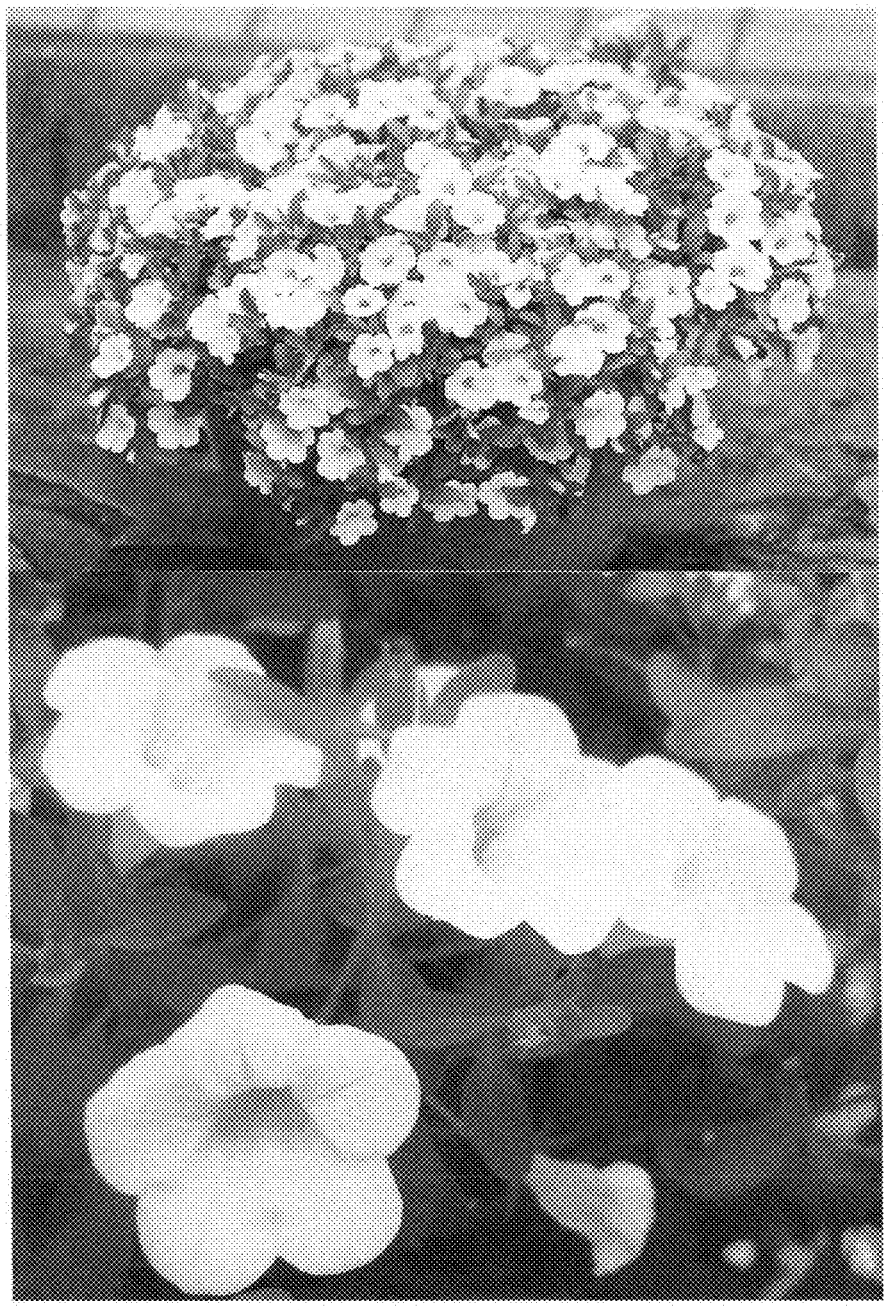

* * * * *